(12) United States Patent
Rao et al.

(10) Patent No.: US 9,921,584 B2
(45) Date of Patent: Mar. 20, 2018

(54) ROUTE EXAMINATION SYSTEM AND METHOD

(71) Applicant: General Electric Company, Schenectady, NY (US)

(72) Inventors: Dattaraj Jagdish Rao, Bangalore (IN); Nidhi Naithani, Bangalore (IN); Anju Bind, Bangalore (IN); Sreyashi Dey Chaki, Bangalore (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/435,458

(22) Filed: Feb. 17, 2017

(65) Prior Publication Data

US 2017/0160746 A1    Jun. 8, 2017

Related U.S. Application Data

(63) Continuation-in-part of application No. 15/075,854, filed on Mar. 21, 2016, now Pat. No. 9,575,007, which is a continuation-in-part of application No. 14/243,933, filed on Apr. 3, 2014, now abandoned.

(51) Int. Cl.
| | |
|---|---|
| *G01J 5/00* | (2006.01) |
| *G05D 1/02* | (2006.01) |
| *G05D 1/00* | (2006.01) |
| *B60W 10/18* | (2012.01) |
| *B60W 10/20* | (2006.01) |
| *B60W 10/22* | (2006.01) |
| *B60W 30/10* | (2006.01) |

(52) U.S. Cl.
CPC ........... *G05D 1/0246* (2013.01); *B60W 10/18* (2013.01); *B60W 10/20* (2013.01); *B60W 10/22* (2013.01); *B60W 30/10* (2013.01); *G05D 1/0088* (2013.01); *B60W 2420/42* (2013.01); *B60W 2710/18* (2013.01); *B60W 2710/20* (2013.01); *B60W 2710/22* (2013.01)

(58) Field of Classification Search
CPC ....... G01N 2021/1765; G06K 9/00664; G06K 9/00805; G06K 9/2018; G06T 2207/10048

See application file for complete search history.

(56) References Cited

U.S. PATENT DOCUMENTS 7,697,727 B2 *   4/2010   Xu ........................ G01C 11/025
                                                          382/108
9,196,048 B2 * 11/2015   Jahanshahi ............. G06T 15/00

* cited by examiner

*Primary Examiner* — Kenneth J Malkowski
(74) *Attorney, Agent, or Firm* — GE Global Patent Operation; John A. Kramer

(57) ABSTRACT

A route examination system includes a thermographic camera configured to be logically or mechanically coupled with a vehicle that travels along a route. The thermographic camera is also configured to sense infrared radiation emitted or reflected from the route and to generate a sensed thermal signature representative of the infrared radiation that is sensed. The system also includes a computer readable memory device configured to store a designated thermal signature representative of infrared radiation emitted from a segment of the route that is not damaged. The system also includes an analysis processor configured to determine a condition of a first portion of the route relative to other portions of the route at least in part by comparing the sensed thermal signature and the designated thermal signature.

4 Claims, 7 Drawing Sheets

ROUTE EXAMINATION SYSTEM AND METHOD

CROSS-REFERENCE TO RELATED APPLICATIONS

This application is a continuation-in-part of U.S. patent application Ser. No. 15/075,854, filed 21 Mar. 2016, which is a continuation-in-part of U.S. patent application Ser. No. 14/243,933, filed 3 Apr. 2014. The entire disclosures of both these applications are incorporated herein by reference.

BACKGROUND

Technical Field

Embodiments of the subject matter disclosed herein relate to examining routes traveled by vehicles for damage to the routes.

Discussion of Art

Routes that are traveled by vehicles may change over time. For example, tracks on which vehicles travel may become broken, cracked, pitted, misaligned, or the like, over time. This damage can pose threats to the safety of the rail vehicles, the passengers located thereon, and nearby persons and property. For example, the risks of derailment of the rail vehicles can increase when the tracks become damaged.

Some known systems and methods that inspect the route, where the route is a set of tracks for a rail vehicle, involve emitting visible markers on the tracks and optically monitoring these markers to determine if the tracks have become misaligned. These visible markers may be created using laser light, for example. But, these systems and methods can require additional hardware in the form of a light emitting apparatus, such as a laser light source. This additional hardware increases the cost and complexity of the systems, and can require specialized rail vehicles that are not used for the conveyance of passengers or cargo. Additionally, these systems and methods typically require the rail vehicle to slowly travel over the tracks so that the visible markers can be examined.

Other known systems and methods inject electric current into the tracks and examining changes to the current to identify open circuits caused by breaks in the tracks. But, these systems and methods may require additional hardware to inject the current and to sense the current, and may be prone to false identifications of damage to the route. It may be desirable to have systems and methods that differ from those that are currently available.

BRIEF DESCRIPTION

In one embodiment, a system (e.g., a route examination system) includes a thermographic camera configured to be logically or mechanically coupled with a vehicle that travels along a route. The thermographic camera is also configured to sense infrared radiation emitted or reflected from the route and to generate a sensed thermal signature representative of the infrared radiation that is sensed. The system also includes a computer readable memory device configured to store a designated thermal signature representative of infrared radiation emitted from a segment of the route that is not damaged. The system also includes an analysis processor configured to determine a condition of a first portion of the route relative to other portions of the route at least in part by comparing the sensed thermal signature and the designated thermal signature.

In one embodiment, a system (e.g., a route examination system) includes a camera or sensor configured to be logically or mechanically coupled with a vehicle that travels along a route. The camera is configured to sense radiation emitted or reflected from the route and to generate a sensed signature representative of the radiation that is sensed from a segment of the route. The system also includes a computer readable memory device configured to store a designated signature representative of radiation emitted from the segment of the route, and an analysis processor configured to compare the sensed signature to the designated signature. The analysis processor is further configured to determine a rate of change to the route based on the comparison of the sensed thermal signature and the designated signature, and to implement one or more actions in response to the rate of change of the route.

In one embodiment, a method (e.g., for examining a route) includes sensing infrared radiation emitted from a route being traveled by a vehicle using a thermographic camera coupled with the vehicle, generating a sensed thermal signature representative of the infrared radiation that is sensed, obtaining a designated thermal signature representative of infrared radiation emitted from a segment of the route that is not damaged, and determining whether the route is damaged by comparing the sensed thermal signature and the designated thermal signature.

BRIEF DESCRIPTION OF THE DRAWINGS

Reference is made to the accompanying drawings in which particular embodiments of the invention are illustrated as described in more detail in the description below, in which.

DETAILED DESCRIPTION

Figure 1:
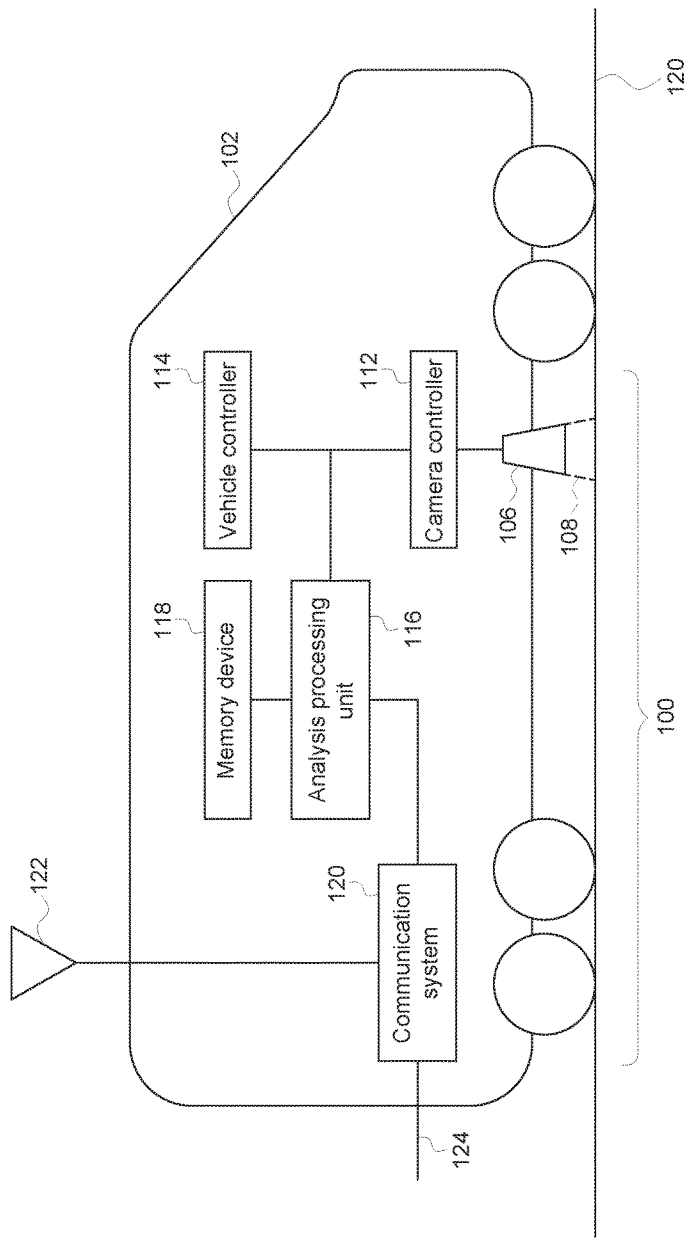
FIG. 1 is a schematic illustration of a thermographic route examination system in accordance with one example of the inventive subject matter described herein.

One or more examples of the inventive subject matter described herein include systems and methods for identifying damaged segments of a route by examining temperatures of the route. Infrared technology can be used to detect thermal signatures in the route.

Examples of routes may include roads, tracks, rails, and the like. The thermal signatures or patterns may be used to differentiate some portions or segments of the route from other portions or segments. In this instance, the first portion may be a damaged or unhealthy portion relative to the other portions of the route proximate to that first portion. The term "healthy" may be used to refer to the lack of damage to the route, while the term "unhealthy" may be used to refer to damage. For example, a healthy segment of a route can include the portion of the route that has no damage or has a sufficiently reduced amount of damage that vehicles can travel on the route at or near an upper speed limit of the route (e.g., track speed). Further, the first (different) portion of the route may be, for example, a pit, pothole, bump, loose debris, crack, buckle, ice patch, leaves, oil slick, or other feature that may affect the travel of the vehicle across that first portion. Different types of routes may have features that are particular to that route. For example, a pair of steel rails may have one type of pitting while a dirt or gravel road may have pits that entirely different (and have correspondingly different thermal signatures).

It may be useful to have external/contextual information about the route itself and/or the environment to better identify the health or type of damage that is likely or possible. As examples, an ice patch (and its signature) may be more likely to occur when the ambient temperature is below freezing, a standing puddle is less likely in the desert, and misaligned rails may be more common on certain track grades or after heavy rains. GPS coordinates may be used in conjunction with map databases to provide more information about particular locations. Known markers, such as paint lines on a road or the ballast/ties of a railroad track, may be used to set baseline values. These known markers may be useful for contextual information as, for example, an identified rail tie would be less likely to be a pitted rail. An edge line on a road might demarcate asphalt from a soft shoulder. Thus, identifying the context allows for both ruling out certain signatures, as well as identifying possible signature types. These additional informational items about the environment may be used in conjunction with the thermal signatures for more accurate decision making and determinations.

In one embodiment, a thermographic or infrared (IR) camera may be mounted on a vehicle, and may be oriented toward the route being traveled upon. As the vehicle moves along the route, infrared images may be captured from the route. The images of the route can be analyzed after the vehicle has passed over the route to obtain heat patterns, or thermal signatures, of the route. The thermal signatures for healthy and unhealthy (e.g., damaged) routes may be compared to identify those segments of the route that may be damaged. Alternatively, the camera or sensor may be logically coupled to the vehicle. That is, it may be mounted to a drone, unmanned aerial vehicle (UAV) or to another vehicle that is further along the route than the subject vehicle. Communication systems may be used to transmit the raw data (for further processing) or the processed thermal signature back to the subject vehicle for further use. These images of the route from the camera or sensor, regardless of whether it is mechanically or logically coupled to the vehicle, may provide the thermal signature information to the subject vehicle in accordance with an embodiment of the invention.

When a damaged segment of the route has been identified, one or more responsive actions may be initiated. For example, a warning signal may be communicated (e.g., transmitted or broadcast) to one or more other vehicles to warn the other vehicles of the condition of the route at the first portion, a warning signal may be communicated to one or more wayside devices disposed at or near the route so that the wayside devices can communicate the warning signals to one or more other vehicles systems, a warning signal can be communicated to an off-board facility that can arrange for the repair and/or further examination of the damaged segment of the route, or the like. In one embodiment, a vehicle may have a responsive suspension system that switches from one mode of operation to another as the vehicle approaches and/or passes over the first portion that has been identified as damaged or unhealthy. The suspension may be stiffened to better absorb shock, the propulsion system may be modified to reduce the chance of skid or slippage, and/or the engine may be throttled down to reduce the vehicle speed, as examples.

FIG. 1 is a schematic illustration of a thermographic route examination system 100 in accordance with one example of the inventive subject matter described herein. The system 100 may be disposed onboard a vehicle 102, such as a rail vehicle. The vehicle can connect with one or more other vehicles, such as one or more locomotives and rail cars, to form a consist that travels along a route 120. In this embodiment the route is a track formed from parallel steel rails. In other embodiments, suitable vehicles may be on-highway vehicles, off-highway vehicles (e.g., a vehicle that may be not designed or may be not designed for travel on public roadways), a passenger automobile (autonomous or otherwise), mining equipment, farming equipment, or the like. For example, the vehicle may be an automobile traveling on a road in one embodiment. In a consist in the current rail-based example, the vehicle can pull and/or push passengers and/or cargo, such as in a train or other system of vehicles.

The system may include one or more cameras 106 mounted or otherwise connected with the vehicle so that the camera moves with the vehicle along the route. Suitable cameras, or sensors, may include thermographic cameras. Note that thermographic cameras are currently contemplated, but other energy spectrums may be used provided that the corresponding signatures and systems accommodate the system. For example, one or more of the cameras may sense light or other radiation emitted from or reflected off of the route. The camera may be oriented such that a field of view 108 of the camera includes a portion of the route. For example, the thermographic camera can be disposed beneath the vehicle as shown in FIG. 1, and/or may be disposed on the front, back, or side of the vehicle and oriented in a generally downward direction toward the route. The field of view of the camera represents the space that may be captured on images generated by the camera.

The camera senses radiation emitted by the route or reflected from the route, or more accurately in some cases by the radiation that is not emitted but should have been. This infrared radiation can represent different temperatures of the route. For a healthy route, the temperatures of different locations in the route may be the same or approximately the same. In one embodiment, a suitable designated range for "normal" may be less than about 2 degrees Celsius. But, for a route portion that differs by more than a threshold value, such as more than 2 degrees Celsius, the analyzer processor may designate such an area as damaged (or just suspect if the temperature differential is barely above the threshold value). The threshold value may be set based on factors that include the time of day, the ambient temperature, the quality of the camera, the cleanliness of any camera lenses, external/contextual information (discussed herein), the type of route, and the type of vehicle and sensitivity of the vehicle to various damaged segments of the route.

Examples of route features that create a temperature differential of more than a threshold value may include breaks through a rail of the route, pitting in the route, and undulations in the route. For example, a break in a rail of the route may include an air gap, which can have a different temperature than the other parts of the rail due to air, condensation, or other debris being inside the air gap. Similarly, pits, cracks, or the like, in the route may be at least partially filled with air, condensation, or debris, which causes the pits, cracks, or the like to have different temperatures than the other parts of the route. Undulations in a rail of the route may cause different locations of the route to be spaced farther from the underlying surface of the ground, ballast material, or the like. These different distances between the rail and the underlying surface can cause different locations of the rail to have different temperatures. The camera may be an infrared camera that senses or otherwise detects the infrared radiation emitted from the route. As a result, the camera senses or otherwise detects the different temperatures of the route.

The camera may sense the infrared radiation from the route while the vehicle may be moving at relatively fast speeds. For example, the infrared radiation may be detected while the vehicle may be moving at or near an upper speed limit of the route, such as the track speed of the route when maintenance may be not being performed on the route or the upper speed limit of the route has not been reduced.

The camera can operate based on signals received from a camera controller 112. The camera controller includes or represents one or more hardware circuits or circuitry that includes and/or may be coupled with one or more computer processors (e.g., microprocessors) or other electronic logic-based devices. The camera controller activates the camera to cause the cameras to sense infrared radiation from the route. The radiation may be emitted or may be reflected from the route surface.

The camera, the camera controller, and/or an analysis processor 116 (described below) generates signatures of the route that represent different temperatures (or other characteristics) of segments or portions of the route. The signatures may be based, at least in part, on the infrared radiation sensed by the camera. For example, the thermal signatures can be infrared images of the route. As described herein, the thermal signatures can indicate different temperatures of different locations of the route, and can be examined to determine where the route may be damaged. And, as mentioned, additional external/contextual information may be brought in to the determination as may be available and appropriate. Optionally, the signatures may represent light emitted or reflected off the route, but not necessarily temperatures.

An analysis processor 116 examines the thermal signatures generated by the camera to identify damaged segments of the route. The analysis processing unit can include or represent one or more hardware circuits or circuitry that includes and/or may be coupled with one or more computer processors (e.g., microprocessors) or other electronic logic-based devices. The analysis processing unit receives the thermal signatures from the camera and examines the thermal signatures to determine if one or more segments of the route may be damaged. As described herein, this examination of the thermal signatures can include comparing a thermal signature from the camera to one or more previously acquired thermal signatures of the route, comparing a thermal signature from the camera to a baseline thermal signature representative of calculated or estimated temperatures of the route, combining a thermal signature with one or more other thermal signatures of the route, or the like. Optionally or additionally, the analysis processing unit can obtain data about the route from one or more other sensors (e.g., other than the camera) and combine or compare this additional data with the thermal signatures from the camera in order to identify and/or predict damage to the route, as described below.

Figure 2:
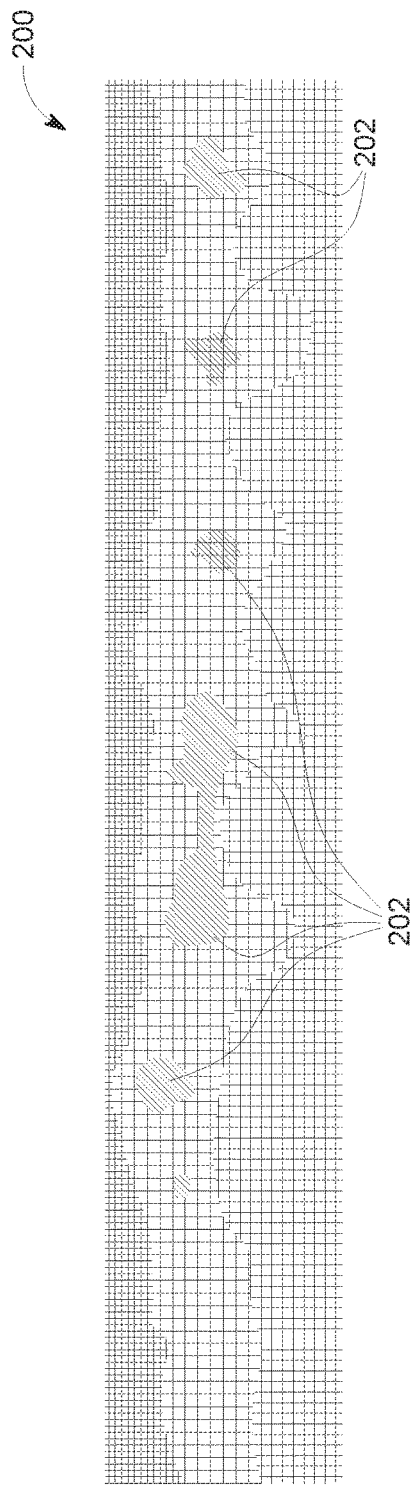
FIG. 2 illustrates a thermal signature of a segment of a route shown in FIG. 1 according to one example of the inventive subject matter described herein.

FIG. 2 illustrates a thermal signature 200 of a segment of the route shown in FIG. 1 according to one example of the inventive subject matter described herein. The thermal signature can include different colors, intensities, or the like, which represent the different temperatures of the segment of the route, as sensed by the camera. In one example, the thermal signature can represent the temperatures of one rail of the route. Another camera may generate another thermal signature for another rail of the route, or one camera may generate thermal signatures for plural rails of the route. The analysis processing unit can examine the thermal signature to identify areas of interest 202 in the thermal signature.

The areas of interest can be identified by determining which portions of the thermal signature have the same or similar (e.g., within a designated range of wavelengths) colors, the same or similar (e.g., within a designated range) intensities, or the like, and which portions of the thermal signature have different (e.g., outside of the designated range) colors, intensities, or the like. In the illustrated example, the areas of interest may have different output values compared to other portions of the thermal signature. Outputs can be represented graphically by colors for human consumption. For example, the areas of interest may have lighter colors (e.g., closer to white than black) and/or brighter intensities than other areas of the thermal signature.

The differences between the areas of interest and the remainder of the thermal signature can indicate that the areas of interest may be representative of damaged portions of the route. For example, the areas of interest may represent hotter locations of the route than other areas in the thermal signature. In one example, the analysis processing unit examines the differences between the areas of interest and other areas of the thermal signature to determine if the areas of interest indicate damage to the route. In one embodiment, hotter areas of interest may represent locations where there may be damage to the route. Alternatively, hotter areas of interest can represent locations where there may be no damage or less damage to the route than other areas of the route. For example, the locations outside of the area of interest may be cooler because the air, debris, or the like, that may be in the cracks, voids, gaps, and the like, in the route may be cooler than the remainder of the route. Damage may be in the form of voids, cracks, gaps, or the like, in the route that may be warmer than other locations of the route. Note, too, that mere "hotter" or "colder" may be the simplest deterministic way of identifying concerns. The patterns of hot and/or cold, the shape of the areas, the gradients from hot to cold, and other external/contextual information may be used to further identify whether there is an unhealthy section of route, and what should be done in response.

In one example, the analysis processing unit can examine several thermal signatures obtained for the same segment or at least partially overlapping segments of the route in order to identify areas of interest in the thermal signatures. The thermal signatures can be formed from the radiation sensed by the camera and/or one or more other cameras when the system and/or one or more other systems travel over the same segment of the route at different times. For example, several thermal signatures of the same segment of the route may be obtained at different times. The analysis processing unit can compare these thermal signatures to identify changes over time in the thermal signatures. The changes may appear as the areas of interest, and may be identified by the analysis processing unit as representative of damage to the route.

Returning to the description of the system shown in FIG. 1, optionally, the analysis processing unit can compare the thermal signature (shown in FIG. 2) generated by the camera with one or more healthy thermal signatures. A healthy thermal signature can represent the thermal signature that was previously obtained from a segment of the route that may be not damaged or may be not significantly damaged (e.g., any damage extends over less than a designated fraction of the segment of the route). For example, during a previous pass of the system over the same segment of the route or over another segment of the route that may be known to not include significant damage, the radiation actually emitted by the segment of the route can be sensed and saved by the system as a healthy thermal signature. In one embodiment, a healthy thermal signature represents a portion of the route that may be not damaged or that does not include any damaged surface, interior, or other part of the route. For example, the healthy thermal signature may be an idealized version of the route that represents the route without any damage.

Figure 3:
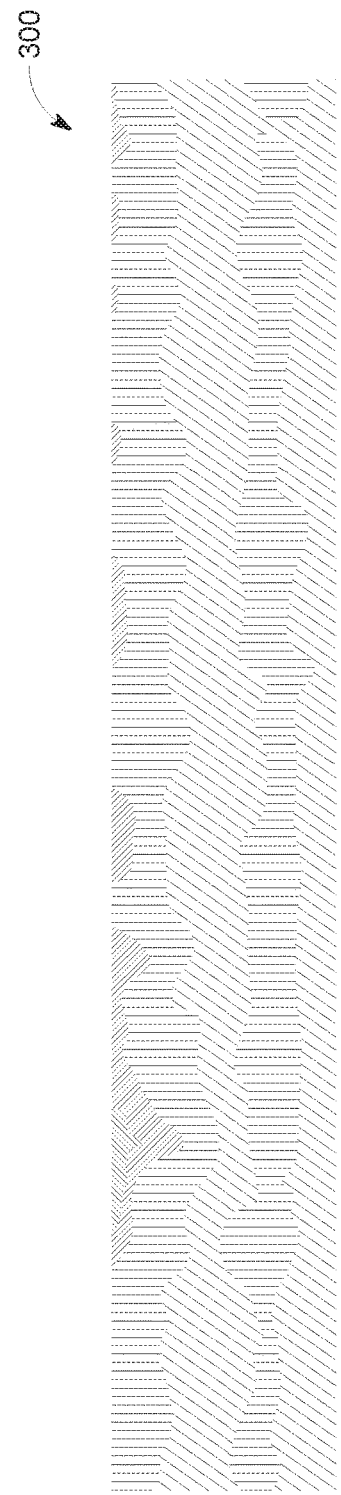
FIG. 3 illustrates another thermal signature of a segment of the route shown in FIG. 1 according to one example of the inventive subject matter described herein.

FIG. 3 illustrates another thermal signature 300 of a segment of the route shown in FIG. 1 according to one example of the inventive subject matter described herein. Similar to the thermal signature shown in FIG. 2, the thermal signature can include different colors, intensities, or the like, which represent the different temperatures of the segment of the route, as sensed by the camera. In one example, the thermal signature can represent the temperatures of one rail of the route. Another camera may generate another thermal signature for another rail of the route, or one camera may generate thermal signatures for plural rails of the route.

One difference between this thermal signature and the first thermal signature (shown in FIG. 2) may be that the thermal signature may be a healthy thermal signature that may be generated from radiation emitted by a segment of the route that does not include significant damage. As described above, the healthy thermal signature may be obtained by a previous pass of the system (shown in FIG. 1) over the segment of the route.

The healthy thermal signature may be stored in a memory device 118 (shown in FIG. 1) of the system. The memory device includes or represents one or more memory devices, such as a computer hard drive, a CD-ROM, DVD ROM, a removable flash memory card, a magnetic tape, or the like. The memory device can be disposed onboard the vehicle or off-board the vehicle. For example, a communication system 120 (shown in FIG. 1) may be disposed onboard the vehicle to allow the vehicle to communicate with one or more off-board components or other vehicles. The communication system includes hardware circuits or circuitry that include and/or may be connected with one or more computer processors (e.g., microprocessors) and communication devices (e.g., wireless antenna 122 and/or wired connections 124) that operate as transmitters and/or transceivers for communicating signals with one or more locations disposed off-board the vehicle. For example, the communication system may wirelessly communicate signals via the antenna and/or communicate the signals over the wired connection (e.g., a cable, bus, or wire such as a multiple unit cable, train line, or the like) to a facility and/or another vehicle system or consist, to another vehicle in the same vehicle system or consist, or the like. If the healthy thermal signature may be not stored onboard the vehicle, then the analysis processing unit can wirelessly obtain or receive the healthy thermal signature from a memory device disposed off-board the vehicle.

Different thermal signatures of healthy route portions may be associated with segments of the route. A vehicle controller 114 (shown in FIG. 1) of the vehicle can be used to manually and/or autonomously control movement of the vehicle, and can track where the vehicle may be located when the thermal signatures may be obtained. For example, the vehicle controller can include and/or be connected with a positioning system, such as a global positioning system (GPS), cellular triangulation system, or the like, to determine where the vehicle may be located at a particular point in time. Optionally, the vehicle controller may determine where the vehicle location based at least in part on how fast the vehicle travels and how long the vehicle has been traveling on the route (a "vector" determination of sorts). For example, the vehicle controller can calculate how far the vehicle has moved from a known location (e.g., a starting location or other location). Yet another way to determine vehicle location is to observe the surround terrain and compare against a known terrain database. Based on the location of the vehicle when the actual thermal signature was obtained, the analysis processing unit can further obtain, from the memory device, a healthy thermal signature associated with the segment of the route at or near the same location of the vehicle.

The analysis processing unit can compare the actual or current thermal signature with the healthy thermal signature to identify differences between the signatures. For example, the areas of interest (shown in FIG. 2) in the actual or current thermal signature may not appear in the same locations as in the healthy thermal signature. Because the healthy thermal signature can represent the radiation that may be expected to be emitted by the segment of the route when the segment does not have significant damage, differences between the actual thermal signature and the healthy thermal signature may indicate locations of damage to the route. For example, because the areas of interest do not appear in the healthy thermal signature but do appear in the actual thermal signature, these areas of interest may be identified by the analysis processing unit as damaged locations of the route.

Optionally, the healthy thermal signature may be a baseline thermal signature. A baseline thermal signature may represent the radiation that may be calculated or estimated as being emitted by the segment of the route at the location of the vehicle when the actual thermal signature (that may be to be examined) was obtained. For example, the radiation that may be expected to be emitted from a healthy segment of the route may be calculated from one or more thermodynamic models or equations representative of the route. The expected radiation can be calculated for different locations of the route and used to create the healthy thermal signature. The analysis processing unit can compare the actual thermal signature to the baseline thermal signature to determine if any differences exist. The differences can represent damage to the route.

Figure 4:
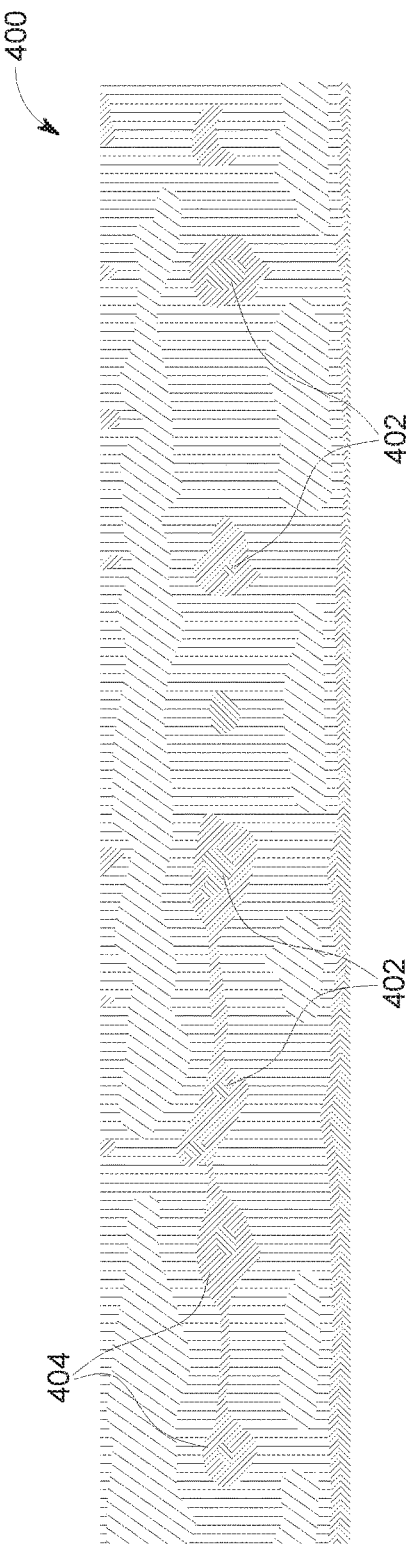
FIG. 4 illustrates a combined thermal signature of a segment of the route shown in FIG. 1 according to one example of the inventive subject matter described herein.

FIG. 4 illustrates a combined thermal signature 400 of a segment of the route shown in FIG. 1 according to one example of the inventive subject matter described herein. Similar to the thermal signatures shown in FIGS. 2 and 3, the thermal signature can include different colors, intensities, or the like, which represent the different temperatures of the segment of the route, as sensed by the camera. In one example, the thermal signature can represent the temperatures of one rail of the route. Another camera may generate another thermal signature for another rail of the route, or one camera may generate thermal signatures for plural rails of the route.

A difference between the thermal signatures described herein may be that a composite thermal signature combines several other thermal signatures of the same or overlapping segments of the route. For example, multiple vehicles may travel over a same segment of a route multiple times and obtain multiple thermal signatures from these travels. One or more previously obtained thermal signatures may be stored on the memory device onboard the vehicle and/or on an off-board memory device. The analysis processing unit can combine the thermal signatures by mixing the thermal signatures together, such as by calculating average, median, deviations, or the like in colors, intensities, or the like, at different locations in the thermal signatures. The averages, medians, deviations, or the like, may then be used to form the combined thermal signature.

The combined thermal signature may be generated to filter out differences between the thermal signatures that may be not due to damage to the route. By calculating averages, medians, deviations, or the like, of several thermal signatures based on emitted radiations that may be measured at different times, the effect of external factors (such as changes in ambient temperatures, weather, or the like) on the combined thermal signature may be reduced. For example, snow, ice, or the like, on the route can mask or hide damage to the route in a thermal signature by reducing elevated temperatures in the thermal signature that may otherwise indicate damage to the route. Similarly, elevated ambient temperatures can raise the temperature of non-damaged portions of the route to appear similar to damaged portions of the route. By combining several thermal signatures obtained at different times (and potentially under different ambient conditions), the impact of external factors that may mask or hide damage to the route can be reduced.

In the illustrated example of the combined thermal signature, several areas of interest 402, 404 have colors and/or intensities that differ from other areas of the signature (e.g., by at least a designated, non-zero threshold amount). The areas of interest in the combined thermal signature may be disposed in the same or approximately the same locations along the route as some of the areas of interest shown in the thermal signature (which also may be referred to as a single-pass thermal signature). As described above, these areas of interest may represent damaged locations of the route. Additional areas of interest may represent damaged locations of the route. These additional areas of interest do not appear in the thermal signature shown in FIG. 2, potentially due to one or more external factors masking or hiding the areas of interest 404 from appearing in the thermal signature.

Figure 5:
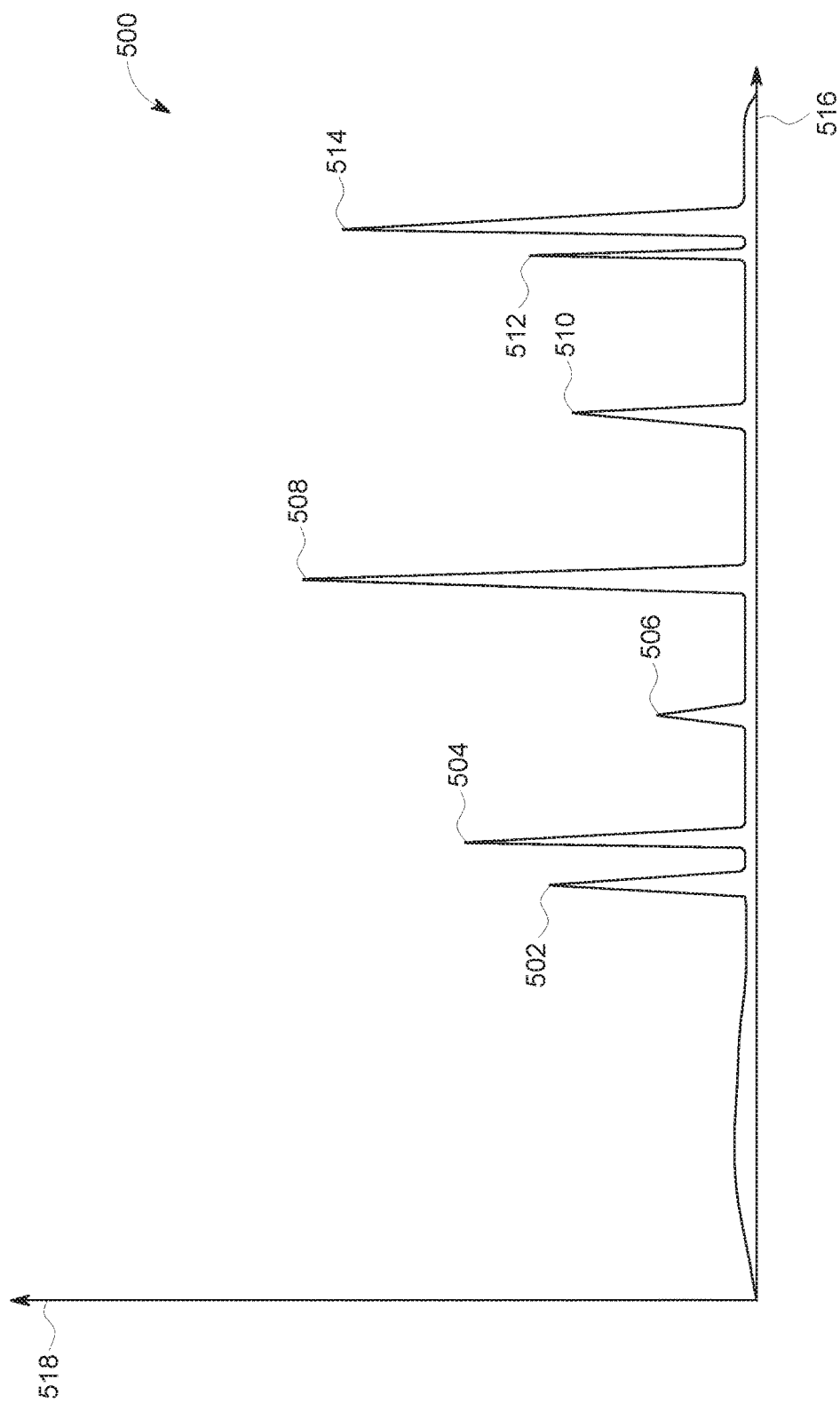
FIG. 5 illustrates a thermal signature of a segment of the route shown in FIG. 1 according to another example of the inventive subject matter described herein.

FIG. 5 illustrates a thermal signature 500 of a segment of the route shown in FIG. 1 according to another example of the inventive subject matter described herein. The thermal signature represents a frequency spectrum of different wavelengths of the radiation emitted by the segment of the route at one or more locations along the route. The thermal signature may be shown alongside a horizontal axis 516 representative of wavelengths of radiation emitted from the route and a vertical axis 518 representative of magnitudes of the wavelengths of the radiation emitted from the route.

The thermal signature includes several peaks 502, 504, 506, 508, 510, 512, 514 representative of an increased presence or magnitude of corresponding wavelengths of the emitted radiation relative to other wavelengths of the emitted radiation. The thermal signature may be generated by the analysis processing unit (shown in FIG. 1). For example, the camera (shown in FIG. 1) may output the radiation sensed from the route to the analysis processing unit, which can then create the thermal signature based on this sensed radiation. Optionally, the camera and/or camera controller (shown in FIG. 1) can generate the thermal signature based on the sensed radiation and output the thermal signature to the analysis processing unit.

The analysis processing unit can examine the thermal signature to determine if the thermal signature indicates damage to the route. For example, the presence or absence of one or more peaks in the thermal signature, and/or the locations or relative locations of the peaks, can represent damage or a lack of damage to the route. The analysis processing unit can compare the presence of the peaks, the locations of the peaks, and the like, to one or more predefined designated peaks associated with damage to the route. If the peaks in the thermal signature match or may be relatively close to the designated peaks, then the analysis processing unit may determine that the route may be damaged.

If the analysis processing unit determines that the route may be damaged, the analysis processing unit can communicate a warning signal to the vehicle controller. This warning signal can indicate to the vehicle controller that the route may be damaged. In response to this warning signal, the vehicle controller may take one or more responsive actions. For example, the vehicle controller may include an output device, such as a display, speaker, or the like, that visually and/or audibly warns an operator of the vehicle of the damaged segment of the route. The operator may then decide how to proceed, such as by slowing or stopping movement of the vehicle, or by communicating with an off-board repair or inspection facility to request further inspection and/or maintenance of the misaligned segment of the route. Optionally, the vehicle controller may automatically implement the responsive action, such as by automatically slowing or stopping movement of the vehicle and/or automatically communicating with the off-board repair or inspection facility to request further inspection and/or maintenance of the damaged segment of the route.

In one embodiment, the processor 114 applies a correlation factor to one or more of the thermal signatures that may be compared with each other. As described above, a combined thermal signature may be generated to filter out differences between the thermal signatures that may be not due to damage to the route. Additionally or alternatively, the processor modifies one or more of the thermal signatures to account for differences between thermal signatures that may be not due to damage to the route. Different portions of the same location of the route appear different in thermographic images due to changes in ambient temperatures. A damaged portion of the route may appear less damaged during cold weather (e.g., snow, ice, or rain) than during warmer weather. Conversely, a non-damaged portion of the route may appear more damaged during warmer weather than during colder weather.

In order to account for these different ambient conditions, the processor modifies one or more of the thermal signatures that may be compared with each other to identify route damage in one embodiment. For example, a first thermal signature may be based on a thermographic image obtained at a first ambient temperature and a second thermal signature may be based on another thermographic image obtained at a warmer, second ambient temperature. The processor modifies the first and/or second thermal signature so that the first and second thermal signatures represent thermal signatures obtained at the same ambient temperatures. The processor can modify a thermal signature by changing an intensity, color, profile, gradient, or other characteristic of a thermographic image on which the thermal signature may be based. For example, the processor can increase the intensities of IR radiation detected in a thermographic image responsive to the thermographic image being obtained at a colder ambient temperature than another thermographic image. Alternatively, the processor can decrease the intensities of IR radiation detected in a thermographic image responsive to the thermographic image being obtained at a warmer ambient temperature than another thermographic image. The processor can determine the ambient temperatures by receiving input from an external source, such as an operator of the vehicle, a thermometer, a communication received from an off-board location via the communication system. The modified thermographic image can be compared with one or more other thermographic images to compare the images and detect damage to the route.

Figure 7:
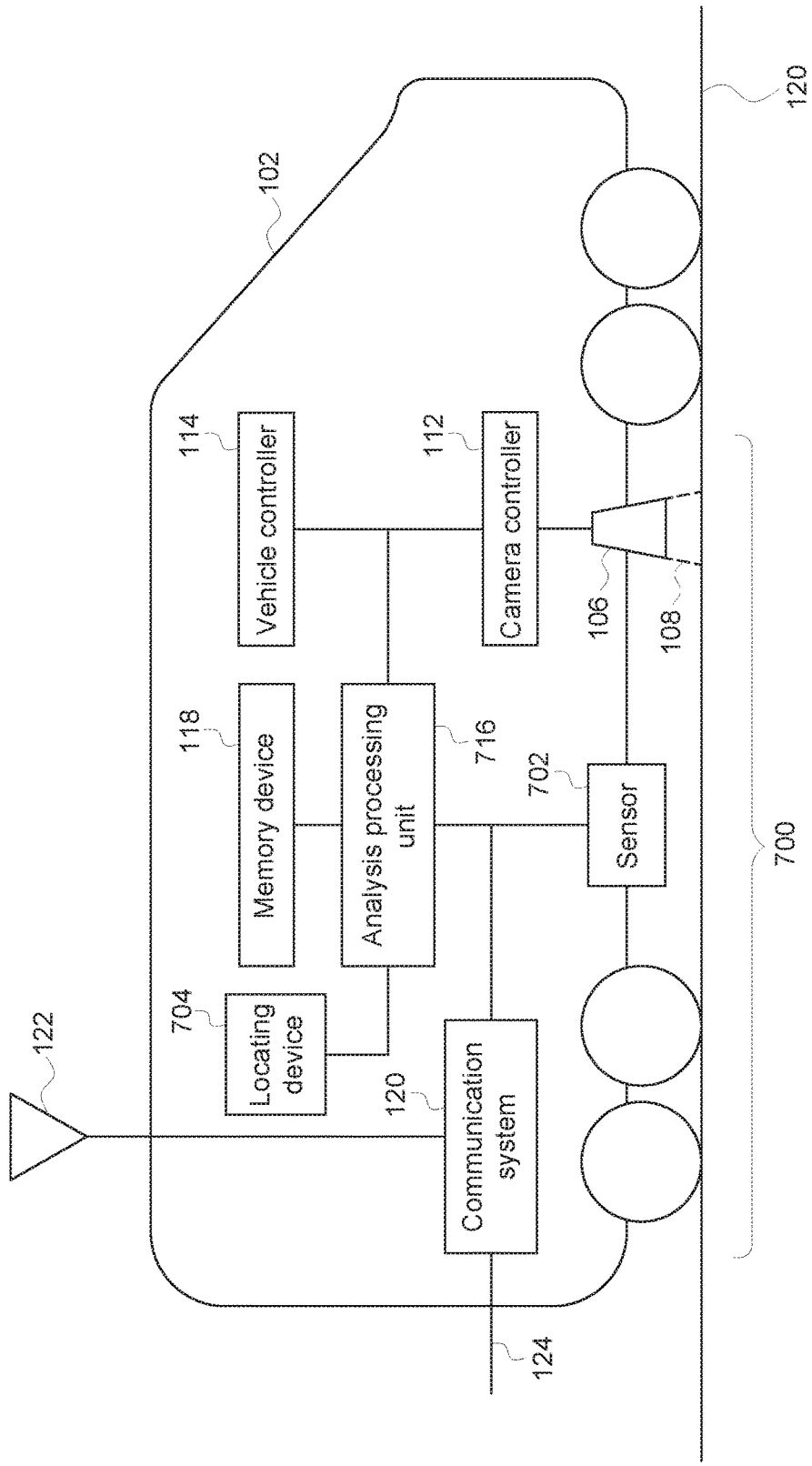
FIG. 7 is a schematic illustration of a thermographic route examination system in accordance with another example of the inventive subject matter described herein.

FIG. 7 may be a schematic illustration of a thermographic route examination system 700 in accordance with another example of the inventive subject matter described herein. The system can be disposed onboard the vehicle, such as a rail vehicle, automobile, or other vehicle, that travels along the route. Similar to the system described above, the system includes one or more thermographic cameras mounted or otherwise connected with the vehicle so that the camera moves with the vehicle along the route. The thermographic camera may be oriented such that the field of view of the camera includes a portion of the route.

The system also includes one or more additional disparate sensors 702 that obtain data about or representative of the route. This additional data differs from the data provided or obtained by the camera. For example, the additional data provided by the sensor may be not thermographic images of the route in one embodiment. As one example, the sensor may be a microphone or other audio pickup device that detects acoustic data (e.g., sounds) generated by movement of the vehicle over the route as the additional data. As another example, the sensor may be a camera other than a thermographic camera that generates images or videos of the route during movement of the vehicle over the route as the additional data. As another example, the sensor includes conductive bodies (e.g., conductive shoes, wires, cables, etc.) that contact a conductive portion of the route (e.g., a rail), inject electric signals into the conductive portion of the route, and detect changes in the signals as the additional data. As another example, the sensor includes a displacement sensor that engages the route and measures changes in a distance between the route and the vehicle as the additional data. Alternatively, the sensor may be another type of sensor that obtains data other than thermographic data.

The camera can operate based on signals received from a camera controller. The camera controller includes or represents one or more hardware circuits or circuitry that includes and/or may be coupled with one or more computer processors (e.g., microprocessors) or other electronic logic-based devices. The camera controller activates the camera to cause the cameras 106 to sense infrared radiation from the route.

An analysis processor 716 examines the data provided by the different sensors to identify damaged segments of the route. The analysis processor can include hardware circuits or circuitry that includes and/or may be coupled with one or more computer processors (e.g., microprocessors) or other electronic logic-based devices. The analysis processor 716 receives the thermal signatures from the camera and the additional data provided by the sensor. The analysis processor compares this data and/or separately examines the data in order to determine if the route may be damaged. As one example, the analysis processor examines the thermal signatures from the camera to identify damage to the route, and also examines the data from the other sensor to determine whether this additional data also indicates damage to the route. In the example where the sensor may be a microphone or other audio pickup device, certain sounds indicate damage to the route. For example, sounds that may be detected at times that the wheels of the vehicle do not pass over known locations of gaps or other breaks in the route (e.g., gaps or insulated joints between segments of a rail) can indicate damage to the route. In the example where the sensor may be a camera other than a thermographic camera, images or video can show damage to the route and can be detected by the processor by comparing the images or video to images or video of a route that may be not damaged, with the differences indicating damage to the route. In the example where the sensor injects electric signals into the conductive portion of the route and detects changes in the signals, the failure to detect the signals or significant decreases in the strength of the signals (e.g., due to a break in the route) indicate damage to the route. In the example where the sensor may be a displacement sensor, significant changes in the distance between the sensor and the route indicate damage to the route, such as breaks in the route that occur when the distance between the sensor and the route change by more than a determine threshold level. In one embodiment, a threshold level may be about 10 percent. Other suitable threshold values may be 15% or 20%, or more. The threshold level may be determined based on application specific parameters.

The processor verifies or refutes damage to the route as detected based on the data obtained by one sensor with the damage as detected based on the data obtained by another sensor. For example, if the data from both sensors indicates a damaged route, then the processor can determine that the route may be damaged. If the data from only one sensor indicates damage to the route, then the processor does not determine that the route may be damaged.

In one embodiment, the processing unit and/or examines data representative of the health of the route obtained at different times. The processing unit can examine thermal signatures or other data about the route that may be obtained at different times, but at the same location along the route, to determine whether the route may be damaged. The memory device in the systems can store previously obtained data and the associated locations where the data may be obtained. The processing unit can determine where the data about the route may be obtained based on information provided by a locating device 704, such as a global positioning system (GPS) receiver, an electromagnetic reader (e.g., radio frequency identification reader) that interrogates roadside transponders encoded with locations along the route, a dead reckoning system that calculates distance traveled along the route based on vehicle speed and an elapsed time, etc. The processing unit can direct the memory device to store the data obtained by the sensor along with the location along the route where the data was obtained. The processing unit can then compare data obtained by the same or different sensors at the same or different times, but representative of the same location along the route, to determine whether the route may be damaged at that location.

In one embodiment, the processor temporally extrapolates the health of the route based on data obtained by the sensor at different times. For example, the health of the route can deteriorate over time. As a result, data obtained by the sensor at an earlier time may not indicate damage or may indicate relatively small amounts of damage to the route compared to the data obtained by the same or different sensor at a later time. Instead of disregarding previously obtained data indicative of less damage to the route, the processor can temporally extrapolate the amount of damage between different times at which data may be obtained by the sensor. This temporal extrapolation can include quantifying amounts of damage to the route based on data obtained by the sensor at multiple different times and extrapolating the damage to the route based on this temporally different data. For example, the damage to the route can be assigned a health score, such as a numerical rating between two values (e.g., zero to one, zero to ten, zero to 100, or another range), with different scores indicating different amounts of damage to the route. In one embodiment, smaller numbers indicate less damage to the route than larger numbers. The processor can assign the scores based on the amount of damage detected. For example, smaller scores may be assigned to locations along the route having no detected damage or damage that may be relatively small (e.g., thermal signatures deviate less from the healthy signatures than for larger scores, the detected sounds may be quieter than for larger scores, the magnitude of the electric signals decreases less than for larger scores, etc.), and larger scores may be assigned to locations along the route having more significant detected damage or damage that may be larger (e.g., thermal signatures deviate more from the healthy signatures than for smaller scores, the detected sounds may be louder than for smaller scores, the magnitude of the electric signals decreases more than for smaller scores, etc.).

The processor obtains sensor data about the same or similar locations along the route (e.g., within the same field of view or sensed area of the sensor 106 and/or 702) at different times (e.g., different hours of the same day, different days, different weeks, different months, different years, etc.), and compares the sensor data or scores of the route to determine how quickly the health of the route may be deteriorating. For example, if the health score of the route at a particular location indicates that the health of the route may be decreasing exponentially, then the processor determines that the health of the route may be deteriorating much faster than another location of the route having a health score that may be linearly decreasing or that may be decreasing at a slower rate. The processor can extrapolate the health scores (or damage to the route) based on the previous health scores to predict the extent of damage to the route at a location in the future.

Based on the rate at which the damage to the route may be worsening and/or the extrapolated damage to the route, the processor implements different responsive actions. For example, for damage to the route at a location that may be worsening at a first rate, the processor may direct the vehicle controller to slow down during travel through that location along the route during current and/or future travel over the route. For damage to the route at a location that may be worsening at a larger, second rate, the processor may direct the communication system to communicate warnings to other vehicles traveling in the vicinity of the location (currently and/or in the future) to notify the other vehicles of the increasing damage to the route. For damage to the route at a location that may be worsening at a larger, third rate, the processor may direct the communication system to communicate a warning to an off-board facility that repairs and/or inspects the route. For damage to the route at a location that may be worsening at a larger, fourth rate, the processor may direct the vehicle controller to no longer travel over that location of the route during future travel of the vehicle.

Figure 6:
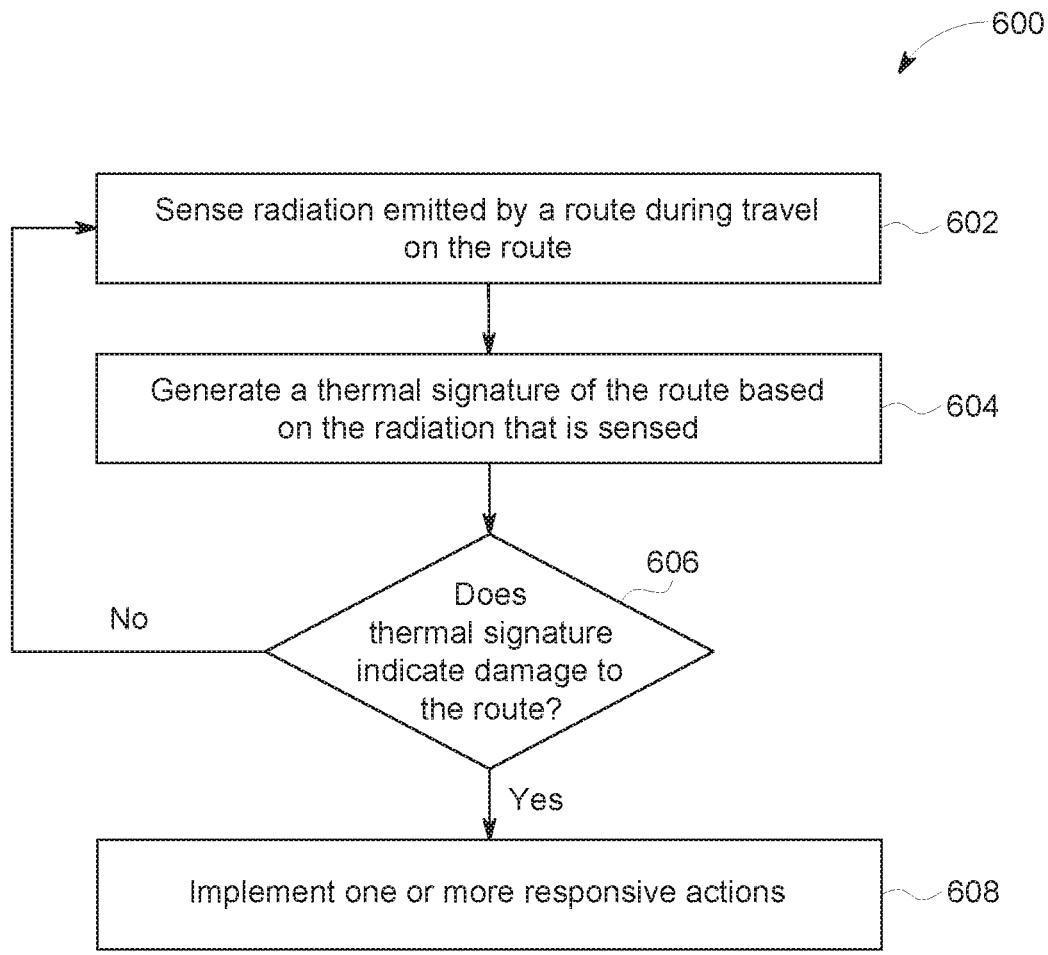
FIG. 6 illustrates a flowchart of a method for examining a route according to one example of the inventive subject matter described herein.

FIG. 6 illustrates a flowchart of a method 600 for examining a route according to one example of the inventive subject matter described herein. The method may be used by the system (shown in FIG. 1) to inspect a route being traveled by a vehicle using one or more thermographic cameras. At 602, radiation emitted by a route may be sensed during movement of a vehicle along the route. As described above, one or more thermographic or infrared cameras may sense temperatures of the route during movement of the vehicle to which the cameras may be connected.

At 604, one or more thermal signatures of the route may be generated from the sensed radiation. For example, a thermal signature that includes different colors, intensities, or the like, associated with different temperatures of the route may be created. Optionally, the thermal signature may be a wavelength spectrum representative of the different temperatures. The thermal signature can be formed from a single pass of the thermographic camera(s) over the route, or may be a combination of several thermal signatures of the same or overlapping segments of the route.

At 606, a determination may be made as to whether the thermal signature indicates damage to the route. As described above, the thermal signature can be examined to identify differences between the colors, intensities, or the like, to locate areas of interest that can represent damage to the route. Optionally, the thermal signature can be combined with several previously acquired thermal signatures to identify such differences representative of damage. In another example, the thermal signature can be compared with a healthy thermal signature and/or a baseline thermal signature to identify differences representative of damage.

If the thermal signature indicates damage to the route, then flow of the method can proceed to 608 and one or more responsive actions can be implemented. For example, a warning signal can be communicated to one or more other vehicles to warn the other vehicles of the damage, a warning signal can be communicated to one or more wayside devices disposed at or near the route so that the wayside devices can communicate the warning signals to one or more other vehicles, a warning signal can be communicated to an off-board facility, movement of the vehicle can be automatically slowed or stopped, an onboard operator can be notified of the damage, or the like.

If the thermal signature does not indicate damage to the route, then flow of the method can return to step 602 so that additional radiation of the route can continue to be monitored.

Figure 8:
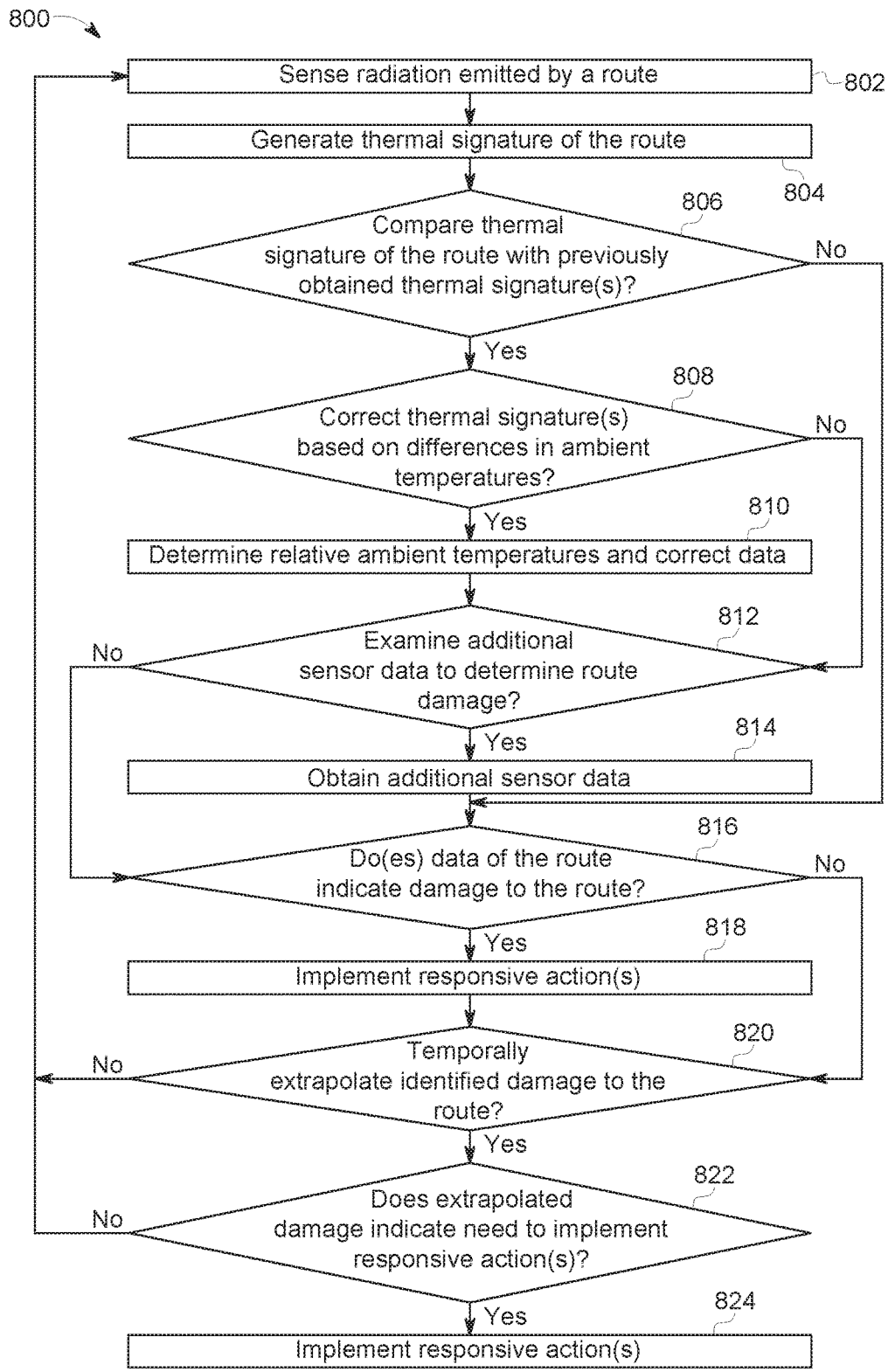
FIG. 8 illustrates a flowchart of one embodiment of a method for examining a route.

FIG. 8 illustrates a flowchart of one embodiment of a method 800 for examining a route. The methods may be used by the systems shown in FIGS. 1 and 7 to inspect a route being traveled by a vehicle using one or more thermographic cameras and, optionally, one or more additional non-thermographic cameras. The flowcharts of the other methods can represent algorithms by which the processors operate, or can be used to create such algorithms for directing operation of the processors in accordance with the operations and functions described herein.

At 802, radiation emitted by or from a route may be sensed during movement of a vehicle along the route. As described above, one or more thermographic or infrared cameras may detect temperatures of the route during movement of the vehicle. These temperatures can be representative of the radiation emitted from the route. At 804, one or more thermal signatures of the route may be generated from the sensed radiation. For example, a thermal signature that includes different colors, intensities, or the like, associated with different temperatures of the route may be created. Optionally, the thermal signature may be a wavelength spectrum representative of the different temperatures. The thermal signature can be formed from a single pass of the thermographic camera(s) over the route, or may be a combination of several thermal signatures of the same or overlapping segments of the route.

At 806, a determination may be made as to whether the thermal signature generated at step 804 may be compared with one or more previously obtained thermal signatures. For example, during a previous trip of the same vehicle or another vehicle over the same segment of a route, thermographic cameras may detect temperatures for creating different thermal signatures. Two or more of these signatures can be compared with each other to identify changes in the health (e.g., damage) of the route. If two or more signatures may be to be compared, then flow of the method can proceed toward step 808. Otherwise, flow of the method can proceed toward 816.

At 808, a determination may be made as to whether to correct one or more of the thermal signatures based on differences in ambient temperatures. As described, the thermal signatures may be obtained at different times and at different ambient temperatures. One thermal signature may be obtained at night when the route may be cooler and another thermal signature may be obtained at noon when the route may be warmer. As another example, one thermal signature may be obtained during the winter when the route may be cooler and another thermal signature may be obtained during the summer when the route may be warmer. If one or more of the thermal signatures may be based on radiation sensed from the route during different ambient temperatures, then the method optionally changes at least one of the thermal signatures to account for this difference. Flow of the method can proceed toward step 810. Alternatively, if the thermal signatures may be not based on radiation sensed during different ambient temperatures, or if the thermal signatures may be not to be modified based on the different ambient temperatures, then flow of the method can proceed toward step 812.

At 810, the different ambient temperatures at which the radiation of one or more of the thermal signatures was obtained may be determined and at least one of the thermal signatures may be modified based on the difference in ambient temperatures. The thermal signatures may be stored by the processor in the memory device (or in an off-board location that may be accessed by the processor via the communication system), with the ambient temperatures at which the radiation represented in the thermal signatures were obtained stored with the thermal signatures. The ambient temperatures can be obtained and compared with each other for the thermal signatures being examined. Depending on the difference between the ambient temperatures, one or more of the thermal signatures may be modified. For example, if a first thermal signature represents radiation obtained at an ambient temperature of 27 degrees Celsius and a second thermal signature represents radiation obtained at an ambient temperature of 12 degrees Celsius, one or more of these thermal signatures may be modified so that the signatures represent radiation from the route at the same temperature. In one embodiment, the intensities of the radiation sensed for the first thermal signature may be reduced to have an average or median radiation that may be the same as an average or median radiation of the sensed radiations for the second thermal signature. In another embodiment, the intensities of the radiation sensed for the second thermal signature may be increased to have an average or median radiation that may be the same as an average or median radiation of the sensed radiations for the first thermal signature. In another embodiment, the intensities of the radiation sensed for the first and second thermal signatures may be increased or decreased, as appropriate, to have the same average or median radiation.

At 812, a determination may be made as to whether additional sensor data may be to be examined (in addition to the thermal signature(s) described above) in order to identify damage to the route. If additional sensor data may be to be examined, then flow of the method can proceed toward step 814. Otherwise, if the thermal signatures may be to be used to detect route damage (and not other types of sensor data), then flow of the method can proceed toward step 816.

At step 814, additional sensor data may be obtained. For example, a non-thermographic camera captures images and/or video of the route, an electric signal may be injected into a conductive rail of the route and changes in the signal may be detected, changes in distances between a sensor or the vehicle and the route may be measured, sounds of travel of the vehicle over the route may be acoustically detected, etc. At step 816, a determination may be made as to whether the acquired data indicates damage to the route. In an embodiment where only a single thermographic image may be used, a thermal signature based on the image may be examined to determine if the route includes pits, cracks, gaps, or other damage, which would appear as changes in the radiation from the route in the signature. In an embodiment where multiple thermographic images may be used, the thermal signatures based on the images (and/or that may be corrected due to differences in ambient temperatures) can be compared with each other or otherwise examined to determine whether the route may be damaged (as described herein). In an embodiment where both a thermal signature and other data of the route may be obtained, the signature can be examined to identify damage to the route and the other data can be examined to confirm or refute the damage, or the other data can be used to identify the damage and the signature can be used to confirm or refute the damage.

If the thermal signature and/or other data indicates that the route may be damaged, flow of the method can proceed toward step 818. Otherwise, flow of the method 800 can proceed toward 820. Optionally, the method 800 can terminate. At 818, one or more responsive actions can be implemented. For example, a warning signal can be communicated to one or more other vehicles to warn the other vehicles of the damage, a warning signal can be communicated to one or more wayside devices disposed at or near the route so that the wayside devices can communicate the warning signals to one or more other vehicles, a warning signal can be communicated to an off-board facility, movement of the vehicle can be automatically slowed or stopped, an onboard operator can be notified of the damage, or the like. Flow of the method may proceed toward step 820 or optionally terminate.

At 820, a determination may be made as to whether damage identified from examination of the thermal signature(s) and/or other data may be to be temporally extrapolated. For example, route damage that may be identified from two or more measurements of the route at different times may be used to determine how quickly the health of the route may be deteriorating, as described above. If such a determination may be to be made, then flow of the method can proceed toward step 822. Otherwise, flow of the method can return toward step 802. Optionally, the method 800 may terminate. The determination made at 820 may be based on whether the previous identifications of damage may be available. For example, if several previous measurements of the health of the route may be available, then the damage may be temporally extrapolated to determine the rate at which the route may be deteriorating, as described above.

At 822, the damage to the route that may be extrapolated from the thermal signatures and/or other data may be examined to determine whether one or more responsive actions may be to be implemented. For example, the previous and/or currently identified extent of damage can be examined to determine how quickly the health of the route may be declining at one or more locations. If the rate of decline of the route may be sufficiently fast (e.g., greater than a designated threshold, such as a rate that may be faster than a route that may be not cracked, pitted, or broken), then one or more responsive actions may be implemented. As a result, flow of the method can proceed toward step 824. Otherwise, flow of the method can return toward step 802 or terminate.

At 824, one or more responsive actions may be implemented. The responsive action(s) that may be performed may be based on the rate of decline of the route. For example, for damage to the route that may be worsening at a first rate, the processor may communicate a signal to direct the vehicle controller to slow down during travel through that location along the route during current and/or future travel over the route. For damage to the route at a location that may be worsening at a larger, second rate, the processor may communicate a signal to direct the communication system to communicate warnings to other vehicles traveling in the vicinity of the location (currently and/or in the future) to notify the other vehicles of the increasing damage to the route. For damage to the route at a location that may be worsening at a larger, third rate, the processor may communicate a signal to direct the communication system to communicate a warning to an off-board facility that repairs and/or inspects the route. For damage to the route at a location that may be worsening at a larger, fourth rate, the processor may communicate a signal to direct the vehicle controller to no longer travel over that location of the route during future travel of the vehicle. Flow of the method may return toward step 802 or may terminate.

In one embodiment, a system (e.g., a route examination system) includes a thermographic camera configured to be logically or mechanically coupled with a vehicle that travels along a route. The thermographic camera is also configured to sense infrared radiation emitted or reflected from the route and to generate a sensed thermal signature representative of the infrared radiation that is sensed. The system also includes a computer readable memory device configured to store a designated thermal signature representative of infrared radiation emitted from a segment of the route that is not damaged. The system also includes an analysis processor configured to determine a condition of a first portion of the route relative to other portions of the route at least in part by comparing the sensed thermal signature and the designated thermal signature.

Optionally, determining the condition of the first portion of the route includes determining that the first portion of the route is damaged, and the analysis processor is configured to direct a vehicle controller of the vehicle to change an operation of the vehicle.

Optionally, the designated thermal signature represents the infrared radiation emitted by the first portion of the route at a common location as the infrared radiation sensed for the sensed thermal signature at a prior time when the first portion of the route was not damaged.

Optionally, the designated thermal signature represents the infrared radiation that one or more of calculated or estimated to be emitted from the first portion of the route.

Optionally, the analysis processor is configured to combine the sensed thermal signature from the thermographic camera with one or more previously sensed thermal signatures and to compare a combination of the sensed thermal signature and the one or more previously sensed thermal signatures with the designated thermal signature to determine whether the first portion of the route is damaged.

Optionally, the analysis processor is configured to determine a rate at which damage to the first portion of the route is changing based at least in part on the sensed thermal signature and one or more previously sensed thermal signatures.

Optionally, the analysis processor is configured to implement different actions in response to the rate at which damage to the first portion of the route is changing based on the rate at which the damage to the first portion of the route is changing.

Optionally, the system also includes one or more sensors configured to measure one or more characteristics of the route that are indicative of damage to the route. The analysis processor optionally is configured to determine that the first portion of the route is damaged responsive to both the sensed thermal signature and the one or more characteristics of the route indicating damage to the first portion of the route.

Optionally, the change to the operation of the vehicle comprises one or more of: autonomously slowing a ground speed of the vehicle, reducing an engine speed of the vehicle, engaging a braking system of the vehicle, steering the vehicle to avoid the first portion of the route, engaging a suspension system of the vehicle to absorb a shock upon contact with the first portion of the route, and/or signaling a maintenance crew to repair the damage to the first portion of the route.

In one embodiment, a system (e.g., a route examination system) includes a camera or sensor configured to be logically or mechanically coupled with a vehicle that travels along a route. The camera is configured to sense radiation emitted or reflected from the route and to generate a sensed signature representative of the radiation that is sensed from a segment of the route. The system also includes a computer readable memory device configured to store a designated signature representative of radiation emitted from the segment of the route, and an analysis processor configured to compare the sensed signature to the designated signature. The analysis processor is further configured to determine a rate of change to the route based on the comparison of the sensed thermal signature and the designated signature, and to implement one or more actions in response to the rate of change of the route.

Optionally, the analysis processor is configured to direct a vehicle controller of the vehicle to autonomously slow movement of the vehicle responsive to the analysis processor determining that the segment of the route is damaged and the location and direction of the vehicle indicate that the vehicle will travel over the segment of the route.

Optionally, the designated signature is a thermal signature of the infrared radiation emitted by, or reflected from, the route at the segment of the at a prior time when the segment of the route was not damaged.

Optionally, the analysis processor is configured to determine that the route is damaged based on both the sensed thermal signature and on external or contextual information.

In one embodiment, a method (e.g., for examining a route) includes sensing infrared radiation emitted from a route being traveled by a vehicle using a thermographic camera coupled with the vehicle, generating a sensed thermal signature representative of the infrared radiation that is sensed, obtaining a designated thermal signature representative of infrared radiation emitted from a segment of the route that is not damaged, and determining whether the route is damaged by comparing the sensed thermal signature and the designated thermal signature.

Optionally, the method also includes autonomously slowing movement of the vehicle responsive to determining that the route is damaged.

Optionally, the designated thermal signature represents the infrared radiation emitted by the route at a common location as the infrared radiation sensed for the sensed thermal signature at a prior time when the route was not damaged.

Optionally, the designated thermal signature represents infrared radiation that is calculated or estimated to be emitted from the route.

Optionally, the method also includes combining the sensed thermal signature from the thermographic camera with one or more previously sensed thermal signatures to form a composite signature, and comparing the sensed thermal signature to the composite signature to determine whether the route is damaged.

Optionally, the method also includes determining a rate at which damage to the route is changing based on comparing a sensed thermal signature to a composite thermal signature.

Optionally, the method also includes implementing one or more different actions selected from (a) communicating one or more of: a warning signal to one or more other vehicles to warn the other vehicles of the condition of the route at the first portion, a warning signal to one or more wayside devices disposed at or near the route so that the wayside devices can communicate the warning signals to one or more other vehicles systems, or a warning signal to an off-board facility that can arrange for the repair or further examination of the damaged segment of the route, and (b) controlling one or more of: a suspension system that switches the vehicle from one mode of operation to another mode of operation as the vehicle approaches or passes over the first portion that has been identified as damaged or unhealthy, the propulsion system to reduce the chance of skid or slippage, or the engine throttle to reduce the vehicle speed.

The above description is illustrative and not restrictive. For example, the above-described embodiments (and/or examples thereof) may be used in combination with each other. In addition, many modifications may be made to adapt a particular situation or material to the teachings of the inventive subject matter without departing from its scope. While the dimensions and types of materials described herein may be intended to define the parameters of the inventive subject matter, they may be by no means limiting and may be exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims may be entitled. In the appended claims, the terms "including" and "in which" may be used as the plain-English equivalents of the respective terms "comprising" and "wherein." Moreover, in the following claims, the terms "first," "second," and "third," etc. may be used merely as labels, and may be not intended to impose numerical requirements on their objects.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter may include other examples that occur to those of ordinary skill in the art. Such other examples may be intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks may be not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion may be explicitly stated. Furthermore, references to "an embodiment" or "one embodiment" of the inventive subject matter may be not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

What is claimed is:

1. A system comprising:
   a sensor configured to be logically or mechanically coupled with a vehicle that travels along a route, the sensor configured to sense radiation emitted or reflected from the route, the sensor configured to generate a first signature representative of the radiation that is sensed from the route; and
   one or more processors configured to compare the first signature with a stored signature of radiation emitted or reflected from an undamaged route, the one or more processors also configured to determine a rate of change to the route based on a comparison of the first signature with the stored signature, and the one or more processors are further configured to implement one or more actions in response to the rate of change of the route, wherein the one or more processors are configured to direct a vehicle controller of the vehicle to autonomously slow movement of the vehicle responsive to the one or more processors determining that the route is damaged.

2. The system of claim 1, wherein the stored signature is a thermal signature of infrared radiation emitted by or reflected from the undamaged route.

3. The system of claim 1, wherein the one or more processor is configured to determine that the route is damaged based on both the first thermal signature and on external or contextual information.

4. The system of claim 1, wherein the stored signature is a combination of previously sensed signatures of the route as sensed by one or more of the sensor or at least one other sensor.

* * * * *